United States Patent
Rubinstein et al.

(10) Patent No.: US 7,247,427 B1
(45) Date of Patent: Jul. 24, 2007

(54) LEPTIN ASSAY

(75) Inventors: Menachem Rubinstein, Rehovot (IL); Batya Cohen, Tel-Aviv (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 588 days.

(21) Appl. No.: 10/110,243

(22) PCT Filed: Oct. 5, 2000

(86) PCT No.: PCT/IL00/00621

§ 371 (c)(1),
(2), (4) Date: Aug. 30, 2002

(87) PCT Pub. No.: WO01/27319

PCT Pub. Date: Apr. 19, 2001

(30) Foreign Application Priority Data

Oct. 10, 1999 (IL) ........................ 132313

(51) Int. Cl.
*C12Q 1/68* (2006.01)
*G01N 33/53* (2006.01)

(52) U.S. Cl. .......... 435/6; 435/7.1; 435/7.92; 435/69.1; 435/325; 435/354; 435/366

(58) Field of Classification Search ........... None
See application file for complete search history.

(56) References Cited

OTHER PUBLICATIONS

Hegen et al., Art. Thromb. Vasc. Biol. 24: 1803-1809, 2004.*
Shyu, et al., "Direct Intramuscular Injection of Plasmid DNA Encoding Angiopoietin-1 but not Angiopoetin-2 Augments Revascularization in the Rabbit Ischenic Hindlimb", *Circulation*, 98(10): 2081-2087 (1998).
Tanaka, et al., "Biologic Significance of Angiopoietin-2 Expression in Human Hepatocellular Carcinoma", *The Journal of Clinical Investigation*, 103(3): 341-345 (1999).
Yoon, et al., "Peroxisome Proliferator-Activated Receptor γ Target Gene Encoding a Novel Angiopoietin-Related Protein Assocoated with Adipose Differentiation", *Molecular and Cellular Biology*, 20(14): 5343-5349 (2000).

* cited by examiner

*Primary Examiner*—Gary Nickol
*Assistant Examiner*—Gyan Chandra
(74) *Attorney, Agent, or Firm*—Browdy & Neimark, PLLC

(57) ABSTRACT

The invention provides a method for determining the presence of leptin in a sample.

14 Claims, No Drawings

LEPTIN ASSAY

FIELD OF THE INVENTION

This present invention relates to assay systems for measuring leptin activity. More specifically the invention relates to in vitro assays for leptin or for agents that mimic the biological activity of leptin (hereinafter: leptin-mimetic agents). The assay is suitable for use in e.g. high throughput screening of libraries of molecules.

BACKGROUND OF THE INVENTION

Obesity, defined as an excess of body fat relative to lean body mass, is associated with important psychological and medical morbidities, the latter including hypertension, elevated blood lipids, and Type II or non-insulin-dependent diabetes mellitus (NIDDM). There are 6-10 million individuals with NIDDM in the U.S., including 18% of the population of 65 years of age (Kamel, H K, et al, Clin. Geriatr. Med., 1999, 15, 265). Approximately 45% of males and 70% of females with NIDDM are obese, and their diabetes is substantially improved or eliminated by weight reduction (Harris 1991, Diabetes Care, 14, 639).

Leptin, the product of the obese gene (Zhang, Y., et al. 1994, Nature 372, 425) functions as a peripheral signal to the brain that regulates food intake and energy metabolism. Leptin is thought to exert its action in the hypothalamus through its receptor, OB-R (Tartaglia, L. A., et al, 1995, Cell 83, 1263). Rodents with mutations that prevent normal expression of either leptin or full-length OB-R are profoundly obese, diabetic, and have a reduced metabolic rate (Coleman, D. L. 1978, Diabetologia 14, 141). However, human obesity does not appear to be associated with mutations in the genes encoding leptin or OB-R (Considine, R. V., et al. 1995, J. Clin. Invest. 95, 2986; Considine, R. V., et al, 1996, Diabetes 19, 992). Although mice with a mutant obese gene can be returned to normal weight by administration of recombinant leptin (Pelleymounter, M. A., et al. 1995, Science 269, 540; Halaas, J. L., et al, 1995, Science 269, 543; Campfield, L. A., et al, Science 269, 546), it seems unlikely that this approach will succeed in obese humans because their serum leptin levels are chronically elevated (Maffei, M., et al, 1995, Nature Med. 1, 1155; Considine, R. V., et al, 1996, N. Engl. J. Med. 334, 292; Sinha, M. K., et al, 1996, J. Clin. Invest. 98, 1277). Obese humans, therefore, appear to be "leptin resistant" (Maffei, M., et al, 1995, Nature Med. 1, 1155; Flier, J. S. & Elmquist, J. K. 1997, Nature Biotech. 15, 20; Campfield, L. A., et al, 1996, Horm. Metab. Res. 28, 619) in that they do not generate a signal commensurate with their serum leptin levels, perhaps because of defective transport of leptin across the blood-brain barrier (Caro, J. F., et al, 1996, Lancet 348, 159) or an inadequate OB-R response. Analysis of OB-R signaling pathways may reveal alternative therapeutic approaches of boosting OB-R responses to overcome leptin resistance and reverse obesity. Leptin and OB-R are members of the four-helical bundle cytokine and receptor superfamilies respectively (Tartaglia, L. A., et al, 1995, Cell 83, 1263; Madej, T., et al, 1995, FEBS Lett. 373, 13). OB-R is most closely related to the gp130 signal transducing receptor that is activated by cytokines such as Interleukin-6 and CNTF, whose signaling pathways have been intensively studied (Kishimoto, T., et al, 1992, Science 258, 593; Stahl, N. & Yancopoulos, G. D. 1994, J. Neurobiology 25, 1454). Leptin receptors are translated as several alternatively spliced products with different cytoplasmic domains (Tartaglia, L. A., et al, 1995, Cell 83, 1263; Lee, G.-H., et al, 1996, Nature 379, 632; Chen, H., et al, 1996, Cell 84, 491; Cioffi, J. A., et al, 1996, Nature Med. 2, 585; Wang, M. Y., et al, 1996, FEBS Lett. 392, 87), but only one isoform, known as the long form or OB-Rb, appears capable of mediating leptin's weight controlling effects (Lee, G.-H., et al, 1996, Nature 379, 632; Chen, H., et al, 1996, Cell 84, 491; Ghilardi, N., et al, 1996, Proc. Natl. Acad. Sci. USA 93, 6231; Baumann, H., et al, 1996, Proc. Natl. Acad. Sci. USA 93, 8374). Obese diabetic (db) mice have a mutation in OB-R that prevents expression of the long OB-R splice isoform, which renders them incapable of appropriately mediating leptin's actions (Lee, G.-H., et al, 1996, Nature 379, 632; Chen, H., et al, 1996, Cell 84, 491).

The discovery of new biologically active molecules, which are used as drugs for the treatment of life-threatening diseases, has involved two basic operations: (i) a more or less random choice of a molecular candidate, prepared either via chemical synthesis or isolated from natural sources, and (ii) the testing of the molecular candidate for the property or properties of interest. The discovery cycle is repeated indefinitely until a molecule possessing the desirable properties is located. In the majority of cases, the molecular types chosen for testing have belonged to rather narrowly defined chemical classes. For example, the discovery of new peptide hormones has involved work with peptides; the discovery of new therapeutic steroids has involved work with the steroid nucleus. As a result, the discovery of new functional molecules, being ad hoc in nature and relying predominantly on serendipity, has been an extremely time-consuming, laborious, unpredictable, and costly enterprise.

Modern theories of biological activity state that biological activities, and therefore physiological states, are the results of molecular recognition events. For example, nucleotides can form complementary base pairs so that complementary single-stranded molecules hybridize, resulting in double- or triple-helical structures that appear to be involved in regulation of gene expression. In another example, a biologically active molecule, referred to as a ligand, binds with another molecule, usually a macromolecule referred to as ligand-acceptor (e.g. a receptor or an enzyme), and this binding elicits a chain of molecular events which ultimately gives rise to a physiological state, e.g. normal cell growth and differentiation, abnormal cell growth leading to carcinogenesis, blood pressure regulation, nerve-impulse-generation and propagation, etc. The binding between ligand and ligand-acceptor is geometrically characteristic and extraordinarily specific, involving appropriate three-dimensional structural arrangements and chemical interactions.

A currently favored strategy for development of agents which can be used to treat diseases involves the discovery of forms of ligands of biological receptors, enzymes, or related macromolecules, which mimic such ligands and either boost (i.e., agonize) or suppress (i.e., antagonize) the activity elicited by the acceptor or receptor. The discovery of such desirable ligands has traditionally been carried out either by random screening of molecules (produced through chemical synthesis or isolated from natural sources, for example, see K. Nakanishi, Acta Pharm. Nord., 1992, 4, 319-328.), or by using so-called "rational" approach involving identification of lead-structure, usually the structure of the native ligand, and optimization of its properties through numerous cycles of structural redesign and biological testing (for example see Testa, B. & Kier, L. B. Med. Res. Rev. 1991, 11, 3548 and Rotstein, S. H. & Mureko, M. A., J. Med. Chem. 1993, 36, 1700). Since most useful drugs have been discovered not through the "rational" approach but through the screening of randomly chosen compounds, a hybrid approach to drug discovery has recently emerged which is based on the use of combinatorial chemistry to construct huge libraries of randomly-built chemical structures which are screened for specific biological activities. (Brenner, S. & Lerner, R. A. Proc. Natl. Acad. Sci. USA 1992, 89, 5381). Any screen of such huge libraries of randomly built chemical structures requires a cost-effective biological assay that is amenable to automation.

Leptin is traditionally assayed in vivo by injecting it to ob/ob mice and observing their reduction in body mass. This bioassay is cumbersome, takes a long time and not reproducible. It is also not suitable for e.g. high throughput screening of libraries containing millions of compounds. Yet, some simpler assay systems were described. For example, the finding that the long form of OB-R contains the sequence YXXQ (Tartaglia, L. A., et al, (1995) Cell 83, 1263), which is a motif that specifies STAT3 activation (Stahl, N., et al, (1995) Science 267, 1349), raised the possibility that STAT3 is critical for mediating leptin responses. Recent results verify that STAT3 is activated both in cultured cells (Ghilardi, N., et al, (1996) Proc. Natl. Acad. Sci. USA 93, 6931; Baumann, H., et al, (1996) Proc. Natl. Acad. Sci. USA 93, 8374; Rosenblum, C. I., et al, (1996) Endocrinology 137, 5178) and in vivo (Vaisse, C., et al, (1996) Nature Gen. 14, 95) by the long form of OB-R, and not by a truncated OB-R or the long form of OB-R with a mutant YXXQ motif (Baumann, H., et al, (1996) Proc. Natl. Acad. Sci. USA 93, 8374; White, D. W., et al, (1997) J. Biol. Chem. 272, 4065). PCT patent application No. WO9857177 proposes the use of STAT3 activation as a basis for a simple in vitro leptin bioassay. However, STAT3 is activated by many other hormones and cytokines, including IL-6, CNTF, interferon alpha and beta, growth hormone and many more cytokines and polypeptide hormones. Therefore, activation of STAT3 can not be used as a specific marker of leptin activity.

PCT application WO9740380 discloses the use of a DNA cassette termed "leptin response element". Attachment of this DNA cassette to a promoter such as the thymidine kinase promoter and a reporter gene such as luciferase will provide a suitable reporter vector. Cells expressing the leptin receptor OB-Rb are transfected with the reporter vector. Such cells are proposed as tools for assay in vitro of leptin. However, according to PCT application WO9740380 the proposed "leptin response element" is identical with the "gamma activation sequence", a well-known element that is activated by many other cytokines, and particularly interferon gamma, interferon alpha and interferon beta. Therefore, assays based on the gamma activation sequence will not be able to discriminate between leptin-mimetic activity and e.g., interferon-mimetic activity.

Still another in vitro assay is based on a chimeric receptor consisting of the extracellular domain of OB-R fused to a transmembrane domain and an intracellular domain of a reporter receptor such as the IL-3 receptor. It is shown that IL-3-dependent cells expressing said chimeric receptor can be used for measuring leptin, which promotes cell proliferation. Thus, upon exposure to leptin, said cells will proliferate and their proliferation may be determined by MTT staining or by incorporation of radiolabelled thymidine (Verploegen S A, et al, 1997, FEBS Lett. 405, 237). This assay system is reliable, it is useful for measuring leptin and is amenable to high throughput screening. However, molecules selected by this high throughput screening based on this assay may not be leptin-mimetic at all. It was shown for instance that a true insulin mimetic agent, found by a high throughput screen acts by interacting with the cytoplasmic domain of the insulin receptor (Zhang B., et al, 1999, Science 284, 974). Therefore, there is a risk that molecules selected by chimeric receptors such as said leptin-IL-3 receptor chimera will interact with the cytoplasmic IL-3-derived domain of the chimera and therefore will be IL-3 mimetic rather than being leptin mimetic. Hence this assay is not reliable for screening of leptin-mimetic agents.

Leptin, the product of the obese gene is expressed in adipocytes and it regulates food intake and energy metabolism through its hypothalamic receptor OB-Rb. Lack of leptin, as in the case of ob/ob mice or lack of OB-Rb, as in the case of db/db mice leads to morbid obesity. However, the most common cases of human obesity are not associated with leptin deficiency. In fact, serum leptin correlates with body mass index and therefore obese individuals have high levels of serum leptin. This correlation led to the notion that obesity is associated with some form of leptin resistance. One possible mechanism of leptin resistance is the inefficient transfer of leptin through the blood brain barrier. Indeed, intracerebroventricular administration of leptin was significantly more effective in reducing adipose tissue mass of rodents as compared with peripheral routes of leptin administration.

Development of leptin-mimetic agents that may cross the blood brain barrier may solve the problem of leptin resistance. For this purpose it is advantageous to screen libraries consisting of low molecular weight agents in order to identify individual agents that exhibit leptin-mimetic activity. Such a screen requires a simple and specific bioassay of leptin activity. So far, as described above, the biological activity of leptin could be determined only by assay in animals. Such assays are cumbersome and therefore not suitable for screening libraries consisting of millions of different substances. Several in vitro assays were described but they are not specific for leptin. Therefore, there is a need to establish a simple and specific assay of leptin's activity that will be easily amenable to automation.

SUMMARY OF THE INVENTION

The present invention thus provides a method determining the presence of leptin or a leptin-mimetic agent comprising contacting a sample with a cell or cell line that expresses Ang-2 in response to leptin and measuring either Ang-2 in the culture medium, cellular RNA encoding Ang-2 or the activation of the Ang-2 promoter.

Preferably a eukaryotic cell or cell line, more preferably a mammalian cell or cell line is employed.

Suitable cell lines are for example differentiated murine adipocyte cell lines, e.g. Swiss 3T3 F442A murine preadipocytes, or human cell lines, e.g. the human marrow stromal cell line hMS2-12.

In accordance with the invention. Ang-2 is measured in a conventional manner in the culture medium by an Enzyme Linked Immunoabsorbent Assay (ELISA) comprising monoclonal and polyclonal antibodies to Ang-2.

Such an ELISA can be adapted for modern screening methods, such as high throughput screening.

The presence of Ang-2 RNA is determined in cultured cells or cell lines by way of reverse-transcription polymerase chain reaction (RT-PCR) in a conventional manner.

Activation of the ANG-2 promoter is detected in accordance with the invention by constructing a construct comprising the Ang-2 promoter region containing a promoter and at least one leptin response element, and a reporter gene operatively linked to the promoter region, preferably placed into an appropriate vector, transfecting a host cell that expresses Ang-2 in response to leptin therewith, incubating with a sample and measuring the reporter gene expression in a conventional manner.

The invention also provides a vector comprising a nucleotide sequence encoding the Ang-2 promoter region containing a promoter and at least one leptin response element, and a reporter gene operatively linked to the promoter region.

DETAILED DESCRIPTION OF THE INVENTION

According to the present invention, methods are disclosed for in vitro assays of leptin. Such methods are suitable for high throughput screening of leptin-mimetic agents. It is disclosed that leptin specifically induces the expression of the angiopoietin-2 gene in cultured adipose cells. High throughput screening of leptin-mimetic agents is achieved by measuring the level of leptin-induced secreted angiopoietin-2 by an Enzyme Linked Immunosorbent Assay (ELISA). Alternatively, leptin activity may be estimated by measuring the activation of the angiopoietin-2 promoter, linked to a reporter gene and inserted into cultured adipose cells.

According to the present invention, methods are disclosed for in vitro assays of leptin. Such methods are also suitable for high throughput screening of leptin-mimetic agents. A co-pending Israeli patent application No. 131739, filed on Sep. 5, 1999 discloses that leptin specifically induces the expression of the angiopoietin-2 gene in cultured adipocytes. No Angiopoietin-2 is expressed in cultured adipocytes in the absence of leptin and the induction of Angiopoietin-2 by leptin is very potent and very specific. Therefore one may measure leptin and leptin-mimetic activity by treating suitable eukaryotic cells with various doses of leptin or leptin-mimetic agents and measuring either Angiopoietin-2 in the culture medium, cellular mRNA encoding Angiopoietin-2 or measuring the activation of the Angiopoietin-2 promoter. Said suitable mammalian cells may be any cell or cell line which expresses angiopoietin-2 in response to leptin treatment. In general, a preferred host cell will be a conveniently cultured eukaryotic, preferably mammalian cell, and in a particularly preferred embodiments it is a differentiated mouse adipocyte cell. A most preferred cell line is Swiss 3T3 F442A murine preadipocytes (Green, H., and Kehinde, O., 1975, Cell 5, 19), which are differentiated into mature adipocytes by maintaining confluent cells in medium supplemented with 10% fetal bovine serum (FBS) for six days. Another most preferred cell line is the human marrow stromal cell line, hMS2-12, which expresses the leptin receptor and may be induced to differentiate to adipocyte (Thomas T., et al, 1999, Endocrinology 140, 1630).

Many available general methods may be adapted by the skilled artisan for the determination of Angiopoietin-2 in the culture medium, cellular mRNA encoding Angiopoietin-2 or for measuring the activation of the Angiopoietin-2 promoter. In one embodiment of the present invention an Enzyme Linked Immunosorbent Assay (ELISA) is developed for the quantitative determination of murine Angiopoietin-2. The ELISA requires to develop a mouse monoclonal antibody for the capture of Angiopoietin-2 to the ELISA plate. The purified monoclonal antibody is used as the first coat of the ELISA plate in order to capture the Ang-2 from the culture supernatant. A polyclonal antibody is raised against Angiopoietin-2 in a host animal (e.g., in rabbit). It should be noticed that the Angiopoietin-2 used in the development of the antibodies should be from the same species as the cell line used for its induction by leptin. For performance of the assay, cells that express Angiopoietin-2 in response to leptin treatment are grown in e.g., 96 well plates. A sample of leptin (positive control) or a putative leptin-mimetic agent is added to the culture and incubation continues for 24-96 hours. Aliquots of the culture media are then removed and transferred to ELISA plates that were pre-coated with said capture monoclonal antibody specific for Angiopoietin-2. The ELISA plates are incubated for 1-16 hours, washed, and said polyclonal antibody to Angiopoietin-2 is added. The ELISA plates are incubated for 1-16 hours, washed and an enzyme-antibody conjugate is added. Typical conjugates are goat-anti rabbit immunoglobulin, conjugated to peroxidase or to alkaline phosphatase. The ELISA plates are incubated for 1-16 hours, washed and developed by addition of a suitable substrate. Said ELISA is suitable for automated high throughput screening.

In another embodiment of the present invention, angiopoietin-2 mRNA is determined in said cultured cells treated with leptin or leptin-mimetic agents. Specific murine Angiopoietin-2 mRNA may be determined by reverse-transcription polymerase chain reaction (RT-PCR). High throughput RT-PCR may be devised, e.g., by using specific "molecular beacons" (Research Genetics, Huntsville Ala., USA). These are single stranded oligonucleotides containing both a fluorescent dye and quencher dye on their 5' and 3' ends, respectively. The oligonucleotide is designed to include a hairpin loop sequence complementary to the sequence of the Angiopoietin-2 cDNA. The oligonucleotide is also designed to include a hairpin stem structure so that when the molecular beacon is not bound to the PCR-amplified Angiopoietin-2 cDNA, the fluorophore is quenched by the 3' quencher dye via energy transfer and no fluorescence occurs. However, if the PCR-amplified Angiopoietin-2 cDNA is added, the complementary loop of the molecular beacon forms a stronger bond with the target PCR product as compared with the stem. This hybridization results in a conformational change forcing the stem apart and resulting in fluorescence (Tyagi S., and Kumar F. R., 1996, Nature Biotech., 16 49).

For performance of the assay, cells that express Angiopoietin-2 in response to leptin treatment are grown in e.g., 96 well plates. A sample of leptin (positive control) or a putative leptin-mimetic agent is added to the culture and incubation continues for 24-96 hours. The plates are washed and total RNA is extracted from the cell monolayer. The RNA is reverse-transcribed using a random primer and the resulting cDNA is subjected to quantitative PCR with specific murine Angiopoietin-2 primers. The amount of the Angiopoietin-2 mRNA is reflected in the amount of the target PCR product, which is measured with the aid of said molecular beacon. All the steps of this assay are suitable for automated high throughput screening.

In another preferred embodiment, the human or murine Angiopoietin-2 promoter is identified and cloned from genomic DNA by means known in the art. Said promoter and a reporter gene are preferably joined in tandem into a replicable mammalian expression vector. However, there may be interviewing sequences present provided they do not interfere with the functioning of the angiopoietin-2 promoter. A reporter gene may be any gene, which encodes a peptide, which is easily detected, or otherwise allows for easy detection of transcription or translation. It generally encodes a protein that does not naturally occur in the host cell or only is produced in small amounts by the host cell. Examples of well known reporter genes include chloramphenicol acetyl transferase (CAT), green fluorescent protein (GFP), luciferase (either bacterial or firefly), and other enzyme-based detection systems such as beta-galactosidase, alkaline phosphatase, and the like. In a particularly preferred embodiment, luciferase is a reporter gene.

The reporter gene construct comprising a) the Angiopoietin-2 promoter region, which contains a promoter and at least one leptin response element and b), the reporter gene operatively linked to the promoter region. It is preferably placed in an appropriate vector that is used to transfect a host cell. The vector may be any known vector, including plasmids, cosmids and viral vectors that can function in a chosen host cell. Such a vector forms yet another aspect of this invention. The host cell may be any cell or cell line that expresses angiopoietin-2 in response to leptin treatment. Such a cell is stably or transiently transfected with said reporter vector. In general, a preferred host cell will be a conveniently cultured eukaryotic, preferably mammalian cell, and in particularly preferred embodiments it is a differentiated mouse adipocyte cell. A most preferred cell line is Swiss 3T3 F442A murine preadipocytes (Green, H., and Kehinde, O., 1975, Cell 5, 19), which are differentiated into mature adipocytes by maintaining confluent cells in medium supplemented with 10% fetal bovine serum (FBS) for six days.

For performance of the assay, a cell or cell line that expresses angiopoietin-2 in response to leptin treatment is stably or transiently transfected with said reporter vector. Said cell is grown in 96 well plates and allowed to differentiate. A sample of leptin (positive control) or a putative leptin-mimetic agent is added to the culture and incubation continues. The level of the reporter gene product is measured in the well after 24-96 hr. In this assay, activation of the Angiopoietin-2 promoter is determined by measuring the gene product of said reporter gene construct. Therefore, the level of the gene product corresponds to that of leptin or a leptin-mimetic activity.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Assay of Leptin and Leptin-Mimetic Agents by ELISA of Angiopoietin-2

Murine Swiss 3T3 F442A cells are grown and differentiated in 96 well plates. A sample of leptin (positive control) or a putative leptin-mimetic agent is added to the culture to a final concentration of 1 microgram/ml and incubation continues for 24 hours. Aliquots of the leptin-induced or leptin-mimetic-induced culture media are then removed and transferred to ELISA plates pre-coated with a capture monoclonal antibody specific for murine Angiopoietin-2. Microtiter plates (Dynatech or Maxisorb, by Nunc) are coated with anti-mouse Angiopoietin-2 monoclonal antibody (serum free hybridoma supernatant or ascitic fluid immunoglobulins) overnight at 4° C. The plates are washed with PBS containing BSA (0.5%) and Tween 20 (0.05%) and blocked in the same solution for at least 2 hrs at 37° C. Aliquots of the leptin-induced or leptin-mimetic-induced culture media are then removed and transferred to ELISA plates (100 microliter/well) for 4 hrs at 37° C. The plates are then washed 3 times with PBS containing Tween 20 (0.05%) followed by the addition of rabbit anti-mouse Angiopoietin-2 serum (1:1000, 100 microliter/well) for further incubation overnight at 4° C. The plates are washed 3 times and a conjugate of goat-anti-rabbit horseradish peroxidase (HRP, Jackson Labs, 1:10,000, 100 microliter/well) was added for 2 hrs at room temperature. The plates are washed 4 times and the color is developed by ABTS (2,2'-azino-bis(3-ethylbenzthiazoline-6-sulfonic acid, Sigma) with $H_2O_2$ as a substrate. The plates are read by an automatic ELISA reader.

Example 2

Assay of Leptin and Leptin-Mimetic Agents by RT-PCR of Angiopoietin-2

Murine Swiss 3T3 F442A cells are grown and differentiated in 96 well plates. Cells are maintained at low serum (0.5%) for 16 hrs prior to stimulation with leptin. Leptin (1 microgram/ml (positive control) or a putative leptin-mimetic agent is added to the culture and incubation continues for 24 hours. The plates are drained and total RNA is isolated with the TRI reagent kit (Molecular Research Center Inc.). Reverse transcription is carried out in 20 microliter volumes using RNase H⁻ reverse transcriptase (SuperScript II, GIBCO-BRL, USA) with 1 μg $(N)_6$ random primer (New England Biolabs, USA). Aliquot (2 microliters) of the reverse transcription product is used for PCR with VENT DNA polymerase (New England Biolabs) and the sense and antisense primers: muAngiopoietin-2 mRNA, AF4326.gb_ro, nucleotides 637-657 and 1147-1167, respectively. The PCR reactions are terminated before saturation. The PCR products are isolated, bought to 1 M NaCl denatured at 72° C. and allowed to hybridize at 52° C. to a molecular beacon whose structure is:

5' rhodamine-GCTGAG-CTGGAGAAGAAGCTGGT-GACA-CTCAGC-3'-dabcyl.

The loop corresponds to nucleotides 898-918 of murine angiopoietin-2 mRNA, Genebank Accession No. AF004326 and the Tm of the stem-loop-structure is 61.6° C. Fluorescent sample represent those cultures that responded to leptin by expressing angiopoietin-2 mRNA.

Example 3

Assay of Leptin and Leptin-Mimetic Agents by a Reporter Vector

Murine Swiss 3T3 F442A pre-adipocytes are stably transfected with a reporter vector consisting of the entire promoter region of murine Angiopoietin-2 in front of a Green Fluorescent Protein (GFP) Gene. The cells are grown in 96 well plates and allowed to differentiate. A sample of leptin (positive control) or a putative leptin-mimetic agent is added to the culture and incubation continues. Appearance of green fluorescence indicates that the cell culture was exposed to leptin or to a leptin-mimetic agent.

Example 4

Assay of Leptin and Leptin-Mimetic Agents by a Reporter Vector

Human hMS2-12 stromal pre-adipocytes are stably transfected with a reporter vector consisting of the entire promoter region of human Angiopoietin-2 in front of a Green Fluorescent Protein (GFP) Gene. The cells are grown in 96 well plates and allowed to differentiate. A sample of leptin (positive control) or a putative leptin-mimetic agent is added to the culture and incubation continues. Appearance of green fluorescence indicates that the cell culture was exposed to leptin or to a leptin-mimetic agent.

The invention claimed is:

1. A method of screening for the presence of a leptin-mimetic agent, comprising contacting a candidate leptin-mimetic agent with a cell or cell line that expresses angiopoietin-2 (Ang-2) in response to leptin and determining the activation of expression from the Ang-2 promoter compared to leptin as a positive control, wherein activation of said promoter identifies the presence of a leptin-mimetic agent.

2. A method according to claim 1, wherein an eukaryotic cell or cell line is employed.

3. A method according to claim 2, wherein the eukaryotic cell or cell line is mammalian.

4. A method according to claim 3, wherein the cell line is a differentiated murine adipocyte cell line.

5. A method according to claim 4, wherein the cell line is Swiss 3T3 F442A murine preadipocytes.

6. A method according to claim 3, wherein the cell line is a human cell line.

7. A method according to claim 1, wherein the activation of expression from the Ang-2 promoter is determined by measuring the amount of Ang-2 produced and secreted in the culture medium.

8. A method according to claim 7, wherein Ang-2 is measured in the culture medium by an immunoassay.

9. A method according to claim 8, wherein Ang-2 is measured in the culture medium by an Enzyme Linked Immunoabsorbent Assay (ELISA) using monoclonal and polyclonal antibodies to Ang-2.

10. A method according to claim 8, adapted for high throughput screening.

11. A method according to claim 1, wherein the activation of expression from the Ang-2 promoter is determined by measuring the amount of cellular RNA encoding Ang-2.

12. A method according to claim 11, wherein presence of Ang-2 RNA is determined in cultured cells or cell lines by way of reverse-transcription polymerase chain reaction (RT-PCR).

13. A method according to claim 1, wherein the activation of expression from the Ang-2 promoter is determined by measuring the amount of a reporter gene product expressed from the Ang-2 promoter.

14. A method according to claim 13, wherein activation of the Ang-2 promoter is determined by constructing a vector comprising the Ang-2 promoter, and a reporter gene operatively linked to the Ang-2 promoter, transfecting a host cell that expresses Ang-2 in response to leptin therewith, incubating with a candidate leptin-mimetic agent and measuring the reporter gene expression.

* * * * *